United States Patent
Kilic et al.

(10) Patent No.: US 7,482,163 B1
(45) Date of Patent: Jan. 27, 2009

(54) METHOD OF ESTIMATING CHEMICAL REACTIVITY OF NANOPARTICLES

(75) Inventors: Cetin Kilic, Mountain View, CA (US); Jangsuk Hyun, Palo Alto, CA (US); Ligen Wang, Palo Alto, CA (US); Mats Larsson, Sunnyvale, CA (US); Juan Cai, Fremont, CA (US); Jifei Jia, Mountain View, CA (US); Xianghong Hao, Sunnyvale, CA (US); Jonathan W. Woo, San Jose, CA (US)

(73) Assignee: Nanostellar, Inc., Redwood City, CA (US)

( * ) Notice: Subject to any disclaimer, the term of this patent is extended or adjusted under 35 U.S.C. 154(b) by 889 days.

(21) Appl. No.: 11/060,850

(22) Filed: Feb. 18, 2005

Related U.S. Application Data

(60) Provisional application No. 60/629,698, filed on Nov. 19, 2004.

(51) Int. Cl.
*G06F 17/50* (2006.01)
*B01J 20/00* (2006.01)

(52) U.S. Cl. ............... 436/37; 502/6; 703/12; 703/2; 700/268

(58) Field of Classification Search ........... 436/37; 502/6; 703/12, 2; 700/268
See application file for complete search history.

(56) References Cited

U.S. PATENT DOCUMENTS 6,106,562 A * 8/2000 Teter et al. .................. 703/12

2002/0086791 A1 * 7/2002 Iglesia et al. ................ 502/6

OTHER PUBLICATIONS

Greeley et al., Computational high-throughput screening of electrocatalytic materials for hydrogen evolution, Nature, vol. 5, Nov. 2006, 909-913.*
Geerlings, P., Chemical Reactivity as Described by Quantum Chemical Methods, Int. J. Mol. Sci., 2002, 3, 276-309.*
U.S. Appl. No. 10/975,646, filed Oct. 28, 2004, Jia et al.
U.S. Appl. No. 11/016,578, filed Dec. 17, 2004, Cai et al.
U.S. Appl. No. 11/062,053, filed Feb. 18, 2005, Cho et al.
K. Honkala et al., "Ammonia Synthesis from First-Principles Calculations," *Science*, Jan. 2005, vol. 307: pp. 555-558.

(Continued)

*Primary Examiner*—Walter D Griffin
*Assistant Examiner*—Christine T Mui
(74) *Attorney, Agent, or Firm*—Patterson & Sheridan, LLP

(57) ABSTRACT

The catalytic efficiency of supported catalysts containing metal nanoparticles is strongly related to the chemical softness at the surfaces of such nanoparticles. The chemical softness of a nanoparticle is obtained using results from Density Functional Theory modeling, an extended version of Embedded Atom Method modeling, and continuum modeling based on size and shape of the nanoparticle. A metal nanoparticle of a certain size and shape is first modeled using the extended EAM and EAM parameters that have been validated with results from DFT modeling, to obtain atomic energy densities at each atom location. The chemical softness value at each atom location is then calculated from the atomic energy densities and various parameters that are derived based on results from DFT modeling. The surface chemical softness value is derived from the local chemical softness values based on the geometry and atomistic structure of the metal nanoparticle.

20 Claims, 5 Drawing Sheets

OTHER PUBLICATIONS

Byeongchan Lee et al., "Atomistic Simulation Study of Controlled Nanostructure Pattterning," *Mat. Res. Soc. Symp. Proc.*, 2003, vol. 775: pp. P9.27.1-P9.27.6.

Byeongchan Lee et al., "Hierarchical Multiscale Study of Metal Nanoparticles," *SES Symposium*, Oct. 2003, Multiscale Simulation Lab, Stanford University, 25 pages.

Alexis T. Bell, "The Impact of Nanoscience on Heterogeneous Catalysis," *Science*, Mar. 2003, vol. 299: pp. 1688-1691.

John B. Butt, "Progress Toward the a Priori Determination of Catalytic Properties," *AIChE Journal*, Jan. 1976, vol. 22(1): pp. 1-26.

J. Cai et al., "Simple Analytical Embedded-Atom-Potential Model Including a Long-Range Force for FCC Metals and Their Alloys," *The American Physical Society, Physical Review B*, Sep. 1996, vol. 54(12): pp. 8398-8410.

C.G. Granqvist et al., "Ultrafine metal particles," *Journal of Applied Physics*, May 1976, vol. 47(5): pp. 2200-2219.

* cited by examiner

METHOD OF ESTIMATING CHEMICAL REACTIVITY OF NANOPARTICLES

RELATED APPLICATION

This application claims the benefit of Provisional Patent Application No. 60/629,698, filed Nov. 19, 2004, entitled "Method of Predicting Chemical Reactivity of Nanoparticles."

BACKGROUND OF THE INVENTION

1. Field of the Invention

The present invention relates to supported catalysts, more specifically to supported catalysts containing nanometer sized platinum particles dispersed throughout the catalyst support material.

2. Description of the Related Art

Many industrial products such as fuels, lubricants, polymers, fibers, drugs, and other chemicals would not be manufacturable without the use of catalysts. Catalysts are also essential for the reduction of pollutants, particularly air pollutants created during the production of energy and by automobiles. The majority of industrial catalysts are composed of a high surface area support material upon which chemically active metal nanoparticles (i.e., nanometer sized metal particles) are dispersed. The support materials are generally inert, ceramic type materials having surface areas on the order of hundreds of square meters/gram. This high specific surface area usually requires a complex internal pore system. The metal nanoparticles are deposited on the support and dispersed throughout this internal pore system, and are generally between 1 and 100 nanometers in size.

The effect of nanoparticle size on catalytic activity is recognized in the current art. An article by Alexis T. Bell entitled, "The Impact of Nanoscience on Heterogeneous Catalysis," Vol. 299, Science, Mar. 14, 2003, teaches that the reactivity and selectivity of catalyst nanoparticles are strongly dependent on their size. FIG. 1 is a diagram from this article which shows that the catalytic activity (in particular, CO oxidation) of Au particles is sensitive to their size and that only particles in the range of 2 to 3 nm are active.

SUMMARY OF THE INVENTION

In addition to size, chemical softness of nanoparticles, in particular, chemical softness at the surfaces of nanoparticles, affects the catalytic efficiency of nanoparticles. The present invention provides a method for modeling the chemical softness of nanoparticles, so that the catalytic efficiency of such nanoparticles can be quantified in a systematic manner.

The supported catalysts containing platinum nanoparticles having average surface softness values (expressed in scaled units ranging from 0 to 1) between 0.07198 and 0.09247 exhibit high catalytic efficiency. The catalytic efficiency of such platinum nanoparticles for CO oxidation, expressed as the turn-over frequency (TOF), expressed as per second/per exposed (surface) atom, was observed to be on or above $0.03062$ s$^{-1}$. By contrast, the TOF of two prior art nanoparticle samples was observed to be 0.02946 s$^{-1}$ and 0.02982 s$^{-1}$, respectively. The supported catalysts containing platinum nanoparticles with tighter average surface softness ranges exhibit even higher catalytic efficiencies. The TOF for CO oxidation of platinum nanoparticles having average surface softness values (expressed in scaled units ranging from 0 to 1) between 0.08031 and 0.08679 was observed to be on or above 0.06554 s$^{-1}$.

The chemical softness of a nanoparticle is obtained using results from Density Functional Theory (DFT) modeling, an extended version of Embedded Atom Method (EAM) modeling, and continuum modeling based on size and shape of the nanoparticle. In the embodiment of the invention described herein, a platinum nanoparticle of a certain size and shape is first modeled using the extended EAM (XEAM) and EAM parameters that have been validated with results from DFT modeling, to obtain atomic energy densities at each atom location. The chemical softness value at each atom location is then calculated from the atomic energy densities and various parameters that are derived based on results from DFT modeling. The surface chemical softness value is derived from the local chemical softness values based on the geometry and atomistic structure of the platinum nanoparticle.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
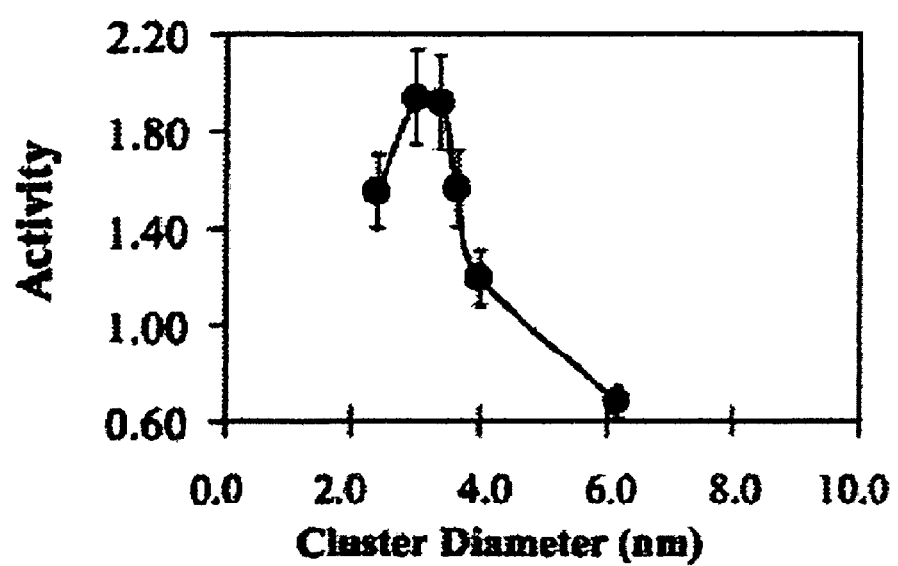
FIG. 1 is a prior art diagram showing the relationship between catalytic activity and nanoparticle size.
Figure 2:
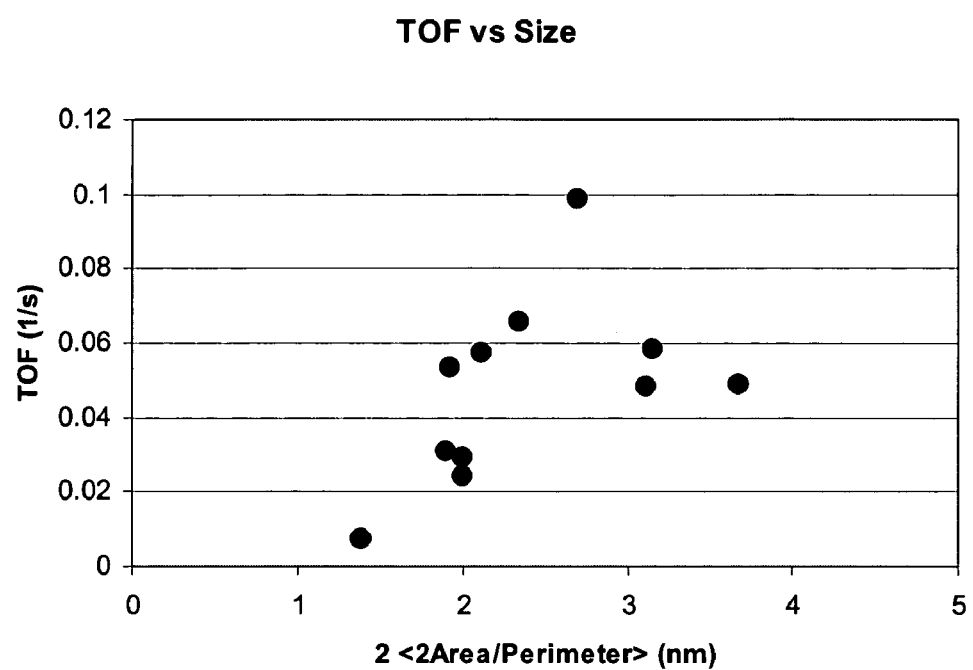
FIG. 2 is a graph showing the catalytic efficiencies of various nanoparticles, including those nanoparticles that are within the scope of the present invention.

FIG. 2 shows the measured TOF for CO oxidation for several platinum nanoparticle batches. These platinum batches represent platinum particles that are part of alumina-supported platinum catalysts that were synthesized according to the methods disclosed in U.S. patent application Ser. No. 10/975,646, filed Oct. 28, 2004, the entire contents of which are incorporated by reference herein. For comparison purposes, the measured TOF for CO oxidation for two prior art samples is also shown.

The physical characteristics of the platinum batches and their measured TOF for CO oxidation are summarized in Table 1 below. The example column identifies the synthesis example that is disclosed in U.S. patent application Ser. No. 10/975,646. The support material for all batches is alumina having a BET surface area of 150 m$^2$/g. Other support materials that may be used to support platinum nanoparticles include silica, oxides of vanadium, oxides of titanium, oxides of zirconium, oxides of iron, cerium oxides, carbon, zeolites, and molecular sieves.

TABLE 1

| Batch | Example | Support | <D> (nm) | Pt loading (wt %) | TOF (s$^{-1}$) |
|---|---|---|---|---|---|
| Prior Art 1 | N/A | alumina | 2.59364 | 0.4 | 0.02982 |
| Prior Art 2 | N/A | alumina | 1.60638 | 0.4 | 0.02946 |
| Pt-48 | 1 | alumina | 1.38462 | 0.4 | 0.00745 |
| Pt-59 | 2 | alumina | 3.68594 | 0.4 | 0.04884 |
| Pt-63 | 5 | alumina | 3.15250 | 0.4 | 0.05855 |
| Pt-64 | 6 | alumina | 1.99450 | 0.4 | 0.02398 |
| Pt-65 | 7 | alumina | 2.15752 | 0.4 | 0.05157 |
| Pt-68 | 8 | alumina | 3.11828 | 0.4 | 0.04845 |
| Pt-69 | 9 | alumina | 2.69794 | 0.4 | 0.09849 |
| Pt-72 | 10 | alumina | 2.34096 | 0.4 | 0.06554 |
| Pt-74 | 11 | alumina | 1.91614 | 0.4 | 0.05340 |
| Pt-76 | 12 | alumina | 2.10924 | 0.4 | 0.05721 |
| Pt-77 | 13 | alumina | 1.98854 | 0.4 | 0.02893 |

The characterization of the platinum batches was carried out by transmission electron microscopy (TEM). Alternatively, scanning transmission electron microscopy (STEM) may be used. Prior to the measurements, a statistically valid sample (about 10-20%) of the platinum metal particles were prepared using the technique described below and disclosed in U.S. patent application Ser. No. 11/016,578, filed Dec. 17, 2004, the entire contents of which are incorporated by reference herein.

First, the alumina-supported catalyst containing platinum particles is ground or milled into fine powder. Then, the powder is mixed into ethynol, and hydrofluoric acid is added to the solvent. The HF acid is effective in separating the platinum particles from the alumina support. The desired concentration of HF in the resulting solution is about 20%, although HF concentration in the range of 10-50% will also work. The resulting solution is then placed in an ultrasonic chamber and ultrasonic waves are generated and applied to the solution for about 1 hour. After letting the solution sit for 12-24 hours, a sample is extracted from the solution and applied to a molybdenum grid that is used by the TEM device. Before the metal grid is placed in the TEM device for imaging, the sample applied to the molybdenum grid is dried.

The average diameter <D> of the platinum batches is estimated as twice the average harmonic parameter. The harmonic parameter is equal to 2×(Area of the nanoparticle observed with TEM)/(Perimeter of the nanoparticle observed with TEM). Dimension measurements made by TEM have an estimated error of about 10%.

The TOF for CO oxidation of the platinum batches was measured in the following manner. The batch is first subjected to a standardized calcining process. The standardized calcining process includes: (1) loading the batch into a reactor; (2) purging the reactor with He at room temperature to remove air in the reactor; (3) heating the batch in 1% oxygen (remainder inert gas) at a rate of 3° C./minute from room temperature to about 500° C.; (4) purging the reactor for 10 minutes with pure He at 500° C. to remove oxygen; (5) purging the reactor in 5% hydrogen (remainder inert gas) for 1 hour at 500° C.; and (6) purging the reactor in pure He while cooling down the reactor to room temperature. Then, without removing the batch from the reactor, the CO oxidation is carried out. The CO oxidation process includes: (1) purging the reactor with the reaction mixture of 1.4% CO, 5.6% $O_2$ (balance He) at room temperature; and (2) heating the reactor from room temperature to 200° C. at about 2° C./minute with the aforementioned $CO/O_2$ mixture. During this heating step, $CO_2$ yield is measured as a function of the temperature.

$$TOF = \frac{\text{Total } CO_2 \text{ yield at } 125° \text{ C.}}{N} \times \frac{N}{N_s}$$

In the equation above, N is the total number of atoms and $N_S$ is the total number of surface atoms. These values are derived using the area measurements from TEM and $r_M$, the metallic radius of the atom.

Table 1 shows that the TOF for platinum batches with similar average diameters, e.g., Pt-64 vs. Pt-74, may vary quite a bit. This indicates that size alone is a poor predictor of catalytic performance of a nanoparticle. The present invention takes into account additional factors with the goal of more accurately predicting the catalytic performance of a nanoparticle. One such additional factor is chemical softness, in particular, the average chemical softness at the surfaces of the nanoparticle (also referred to herein as "average surface softness").

Figure 3:
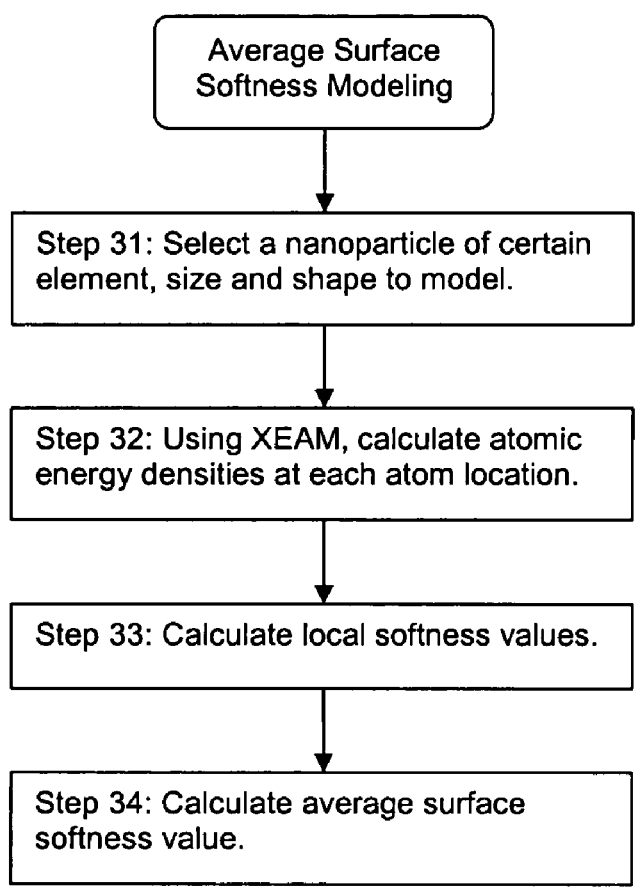
FIG. 3 is a flow diagram that illustrates the process steps carried out to calculate an average surface softness of a nanoparticle.

The process for determining the average surface softness is illustrated in the flow diagram of FIG. 3. In step 31, a nanoparticle of a certain element is selected for modeling. The crystal structure of the selected element is taken from available crystallographic tables at the elemental energy ground state. The element may be any element, including platinum, silver, copper, palladium and any other metallic element that is commonly used as a catalyst metal. The size corresponds to the size of the actual synthesized sample that is being analyzed, as determined from TEM characterization of a statistically valid sample (e.g., 10-20%) described above, or a theoretical sample that is being modeled. The shape corresponds to the shape of the selected element at its ground state. For platinum, this shape is truncated octahedron. Based on the element and its crystal structure, size and shape, the number of atoms and the geometric locations of the atoms of the nanoparticle can be derived.

In step 32, the atomic energy density at each atom location of the nanoparticle, $E_i$, is calculated using an extended version of the EAM. The EAM provides the following formulations for $E_i$:

$$E_i \sum_{j(\neq i)} \Phi(R_{ij}) + F_i(\rho_i)$$

The XEAM extends the above formulations for the EAM in the following manner:

$$E_i = \sum_{j(\neq i)} V(r_{ij}) + \left(1 - 0.5 * \frac{\rho_i^{asym}}{\rho_i}\right) F_i(\rho_i)$$

The function $\Phi(R_{ij})$ is the pair potential function in the EAM formulation and the function $F_i(\rho_i)$ is the embedding function in the EAM formulation. The symbol, $\rho$, represents the (modeled) charge density function. The function, $\rho_i$, represents the charge density function at atom location i, and the function, $\rho_i^{asym}$, represents the asymmetric charge density function at atom location i. The formulations of $\rho_i$ and $\rho_i^{asym}$ are set forth below:

$$\rho_i = \sum_{j(\neq i)} \rho_j^a[R_{ij}]; \text{ and } \rho_i^{asym} = \left\| \sum_{j(\neq i)} \rho_j^a[R_{ij}] \frac{R_{ij}}{\|R_{ij}\|} \right\|$$

where $\rho_j^a$ is the charge density contribution coming from site j to the atom at site i. A total of five EAM parameters are used in the EAM. They are: $\chi$, $\alpha$, $\beta$, $F_1$ and $r_a$. The use of these parameters in accordance with EAM and as applied to seven face-centered cubic (fcc) metals (Al, Ag, Au, Cu, Ni, Pd, and Pt) and their binary alloys is described in an article by J. Cai and Y. Ye, "Simple analytical embedded-atom-potential model including a long-range force for fcc metals and their alloys," Phys. Rev. B, Vol. 54, p. 8398 (1996), the entire contents of which are incorporated by reference herein.

In the embodiment of the invention described herein, these parameters are derived to reproduce the energy density computed using DFT modeling and have the following values for platinum:

$\chi$=4.3 Å$^{-1}$;

$\alpha$=0.4033 eV;

$\beta$=5.6379;

$F_1$=0.6815 eV; and $r_a$=2.3839 Å.

In step 33, the chemical softness at each atom location of the nanoparticle, $s_i$ is calculated using the following formulation:

$$s_i = s_{gs} + (s_{at} - s_{gs}) \sum_{n=1}^{5} C_n \left( \frac{E_i - E_{gs}}{E_{at} - E_{gs}} \right)^n$$

where:

the chemical softness, $s_i$, is unit-less;

$s_{gs}$ is the softness for the bulk atoms (set to 0);

$s_{at}$ is the softness of a free atom is derived experimentally or it may be calculated using DFT; this value is set to 1 and all other softness values are scaled with respect to this value;

$\{C_1, C_2, C_3, C_4, C_5\}$ are universal constants that are used to model any element including platinum;

$C_1$=0.00031671;

$C_2$=2.03164;

$C_3$=−0.0198892;

$C_4$=−6.60821; and $C_5$=5.04367.

$E_{gs}$ is the atomic energy density for the bulk atoms (this value is different for different metals; for platinum, $E_{gs}$=−5.7 eV, but for silver, $E_{gs}$=−2.8 eV); and $E_{at}$ is the atomic energy density for a free atom (set to 0).

In step 34, the average surface softness is derived from the local chemical softness values based on the geometry and atomistic structure of the nanoparticle. As part of this derivation, the computed local softness value for each atom, $s_i$, is first distributed around that value using a Gaussian distribution with a spread, $\sigma$, to model the surface imperfections due to temperature. The spread, $\sigma$, is zero for ideal conditions (e.g., T=0° K). Otherwise, the spread, $\sigma$, is equal to $k_B$*T, where $k_B$ is the Boltzmann constant and T is temperature in ° K at which $CO_2$ yield is measured to compute TOF. The Gaussian distributions are then summed to produce the softness profile N(s) that specifies the number of atoms (N) corresponding to a softness value, s. The softness profile, N(s), can be expressed in the following equation form:

$$N(s) \sum_{i=1}^{Ntotal} \frac{1}{\sigma \sqrt{2\pi}} \exp\left( -\frac{|s-s_i|^2}{2\sigma^2} \right)$$

where Ntotal is the total number of atoms in the nanoparticle being modeled.

The average surface softness, $s_{avg}$, is derived from the softness profile, N(s), using the following equation:

$$S_{avg} = \frac{\int ds f(s) s N(s)}{\int ds f(s) N(s)}$$

where f(s) is the filtering function that filters out the softness values associated with the bulk atoms.

Figure 4:
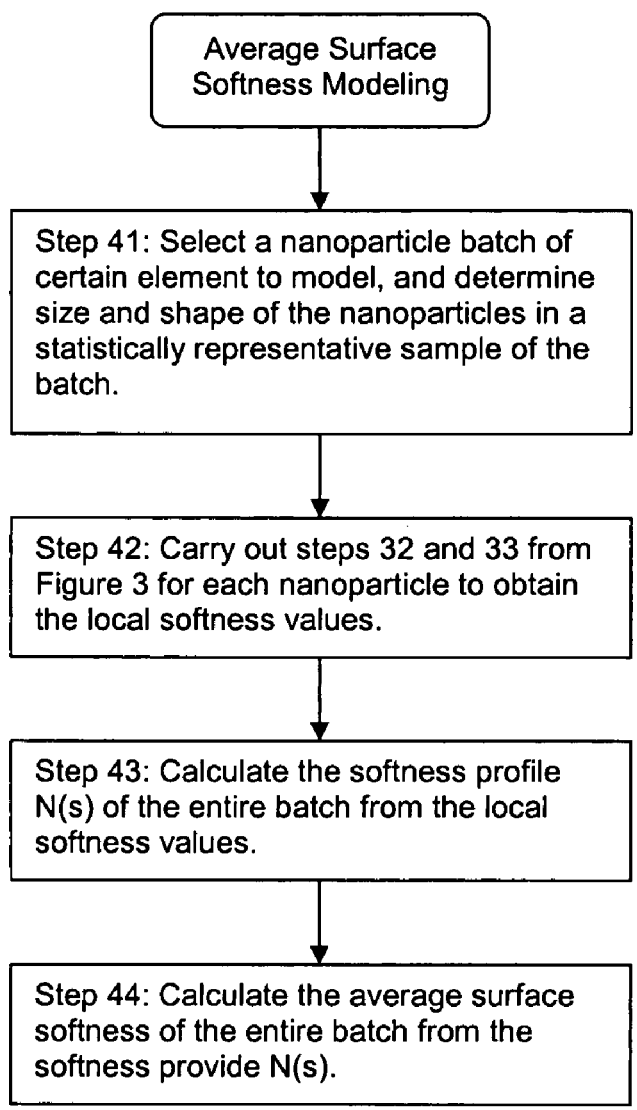
FIG. 4 is a flow diagram that illustrates the process steps carried out to calculate average surface softness of a nanoparticle batch.

The process for determining the average surface softness of a nanoparticle batch is illustrated in the flow diagram of FIG. 4. In step 41, a nanoparticle batch of a certain element is selected for modeling. The element may be any element, including platinum, silver, copper, palladium and any other metallic element commonly used as a catalyst metal. The size distribution of the nanoparticles in the batch is determined from TEM characterization of a statistically valid sample (about 10-20%) as described above. The shape of the nanoparticles in the batch is assumed to be the lowest energy state shape. When modeling platinum nanoparticles, the shape is assumed to be truncated octahedron, which has the lowest energy state. The number of atoms and the geometric locations of the atoms of any one nanoparticle in the sample can be derived based on that nanoparticle's element, crystal structure, size, and shape.

In step 42, the process steps 32-33 of FIG. 3 are carried out for each of the nanoparticles. Then, in step 43, the softness profile, N(s), is calculated from the local softness values obtained in step 42. In step 44, the average surface softness of the nanoparticle batch is calculated based on the softness profile.

Figure 5:
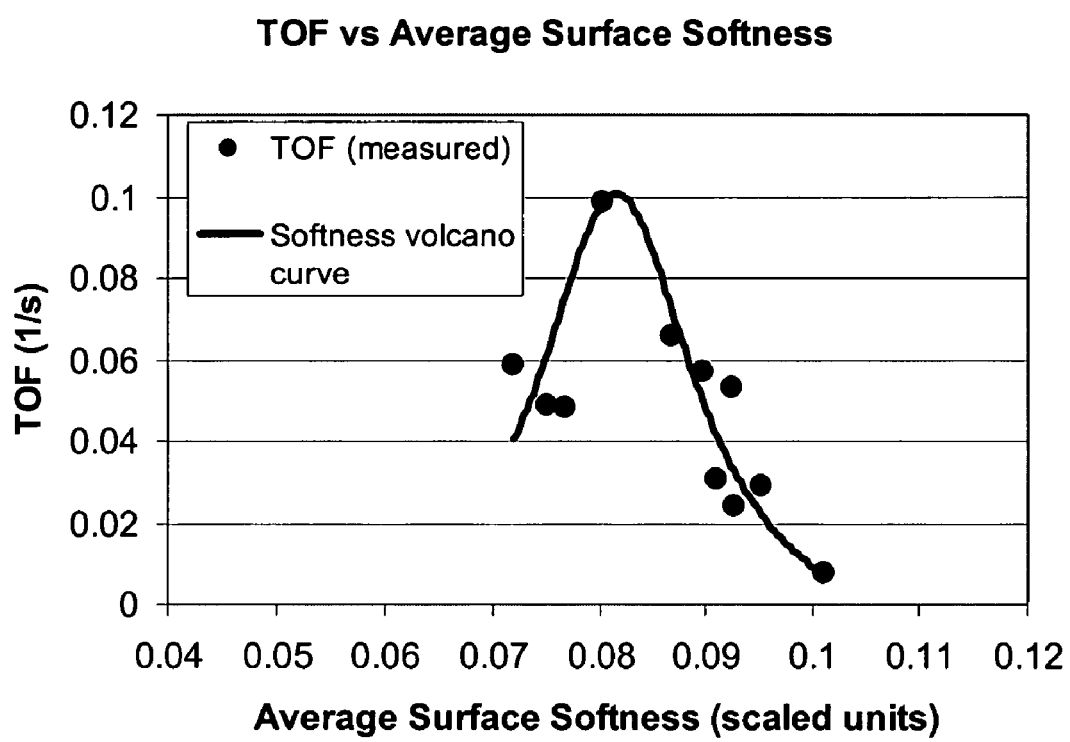
FIG. 5 is a graph showing the effect of surface softness on catalytic efficiency.

The TOF curve plotted against surface softness exhibits a volcano curve in the shape of a Lorentzian function. Table 2 shows different platinum nanoparticle batches and the resulting average surface softness values (expressed in scaled units ranging from 0 to 1) that fall on the volcano curve in the shape of a Lorentzian function. The "TOF vs. softness" volcano curve is shown in FIG. 5.

TABLE 2

| Batch | Example | Support | <D> (nm) | TOF (s$^{-1}$) | <surface softness> |
|---|---|---|---|---|---|
| Pt-48 | 1 | alumina | 1.38462 | 0.00745 | 0.10110 |
| Pt-59 | 2 | alumina | 3.68594 | 0.04884 | 0.07516 |
| Pt-63 | 5 | alumina | 3.15250 | 0.05855 | 0.07198 |
| Pt-64 | 6 | alumina | 1.99450 | 0.02398 | 0.09274 |

TABLE 2-continued

| Batch | Example | Support | <D> (nm) | TOF (s⁻¹) | <surface softness> |
|---|---|---|---|---|---|
| Pt-65 | 7 | alumina | 2.15752 | 0.05157 | 0.07818 |
| Pt-68 | 8 | alumina | 3.11828 | 0.04845 | 0.07674 |
| P1-69 | 9 | alumina | 2.69794 | 0.09849 | 0.08031 |
| Pt-72 | 10 | alumina | 2.34096 | 0.06554 | 0.08679 |
| Pt-74 | 11 | alumina | 1.91614 | 0.05340 | 0.09247 |
| Pt-76 | 12 | alumina | 2.10924 | 0.05721 | 0.08973 |
| Pt-77 | 13 | alumina | 1.98854 | 0.02893 | 0.09530 |

While particular embodiments according to the invention have been illustrated and described above, those skilled in the art understand that the invention can take a variety of forms and embodiments within the scope of the appended claims.

What is claimed is:

1. A method of estimating chemical reactivity of a particle, comprising the steps of:
   determining size and shape of the particle;
   approximating atomic energy densities at various locations of atoms in the particle;
   calculating local chemical softness values at said various locations of atoms based on the atomic energy densities;
   calculating an average surface chemical softness of the particle based on the local chemical softness values; and
   estimating the chemical reactivity of the particle based on the average surface chemical softness value of the particle.

2. The method according to claim 1, wherein the shape of the particle is approximated as the shape of the particle at its ground state.

3. The method according to claim 2, wherein the particle comprises platinum and the shape of the particle is truncated octahedron.

4. The method according to claim 1, further comprising the step of determining the number of atoms and geometric locations of said atoms based on the size and shape of the particle.

5. The method according to claim 1, wherein the particle comprises platinum and the local chemical softness values are further based on the chemical softness of a free platinum atom and the atomic energy density of bulk platinum atoms.

6. The method according to claim 1, wherein the atomic energy densities are approximated using an embedded atom method.

7. The method according to claim 6, wherein parameters used in the embedded atom method are derived to reproduce the energy densities computed using DFT modeling.

8. The method according to claim 1, wherein the chemical reactivity data comprises catalytic activity data, and the catalytic activity data of the particle is estimated based on catalytic activity data of other particles with similar average surface chemical softness values.

9. A method of estimating chemical reactivity of a metal particle batch, comprising the steps of:
   extracting a statistically valid sample of the metal particle batch;
   determining size and shape of each of the particles in the sample;
   for each particle in the sample, calculating local softness values at various atom locations;
   calculating an average surface softness of the metal particle batch based on the local softness values of the particles in the sample; and
   estimating the chemical reactivity of the metal particle batch based on chemical reactivity data of other metal particle batches with similar average surface softness value.

10. The method according to claim 9, wherein each step of calculating the local surface softness values comprises the steps of:
    approximating atomic energy densities at various locations of atoms in the particle; and
    calculating local softness values at said various locations of atoms based on the atomic energy densities.

11. The method according to claim 10, wherein the metal particle comprises platinum and the local chemical softness values are further based on the chemical softness of a free platinum atom and the atomic energy density of bulk platinum atoms.

12. The method according to claim 10, wherein the atomic energy densities are approximated using an embedded atom method.

13. The method according to claim 9, wherein the shape is truncated octahedron.

14. A method of estimating catalytic efficiency of a metal particle, comprising the steps of:
    calculating an average surface softness of the metal particle based on the structure of the metal particle;
    measuring the catalytic efficiency of various samples of the metal particle having different structure;
    calculating average surface softness of each of the various samples; and
    estimating the catalytic efficiency of the metal particle based on the average surface softness of the metal particle and the relationship of the catalytic efficiency to the average surface softness of the various samples.

15. The method according to claim 14, wherein the measured catalytic efficiency comprises turn-over frequency.

16. The method according to claim 15, wherein the step of measuring comprises the steps of
    subjecting each sample to CO oxidation and measuring the $CO_2$ yield; and
    deriving TOF based on the total $CO_2$ yield divided by the number of surface atoms on the sample.

17. The method according to claim 16, wherein the step of measuring further comprises the step of determining the number of total atoms in the sample and the TOF is derived based on the number of total atoms in the sample and TEM characterizations of area and perimeter of the samples.

18. The method according to claim 14, wherein each step of calculating the average surface softness comprises the steps of:
    approximating atomic energy densities at various locations of atoms in the metal particle;
    calculating local chemical softness values at said various locations of atoms based on the atomic energy densities; and
    calculating the average surface chemical softness of the metal particle based on the local chemical softness values.

19. The method according to claim 18, wherein the metal particle comprises platinum and the local chemical softness values are further based on the chemical softness of a free platinum atom and the atomic energy density of bulk platinum atoms.

20. The method according to claim 18, wherein the atomic energy densities are approximated using an embedded atom method.

* * * * *